US012679810B2

(12) United States Patent
Feng et al.

(10) Patent No.: US 12,679,810 B2
(45) Date of Patent: Jul. 14, 2026

(54) METHOD FOR THE PREPARATION OF SULFINPYRAZONE

(71) Applicant: CHENGDA PHARMACEUTICALS CO., LTD., Jiaxing (CN)

(72) Inventors: Yu Feng, Jiaxing (CN); Wei Qian, Jiaxing (CN); Yanping Xu, Jiaxing (CN); Liyan Gao, Jiaxing (CN); Weihui Zhong, Jiaxing (CN); Fei Ling, Jiaxing (CN); Tao Liu, Jiaxing (CN)

( * ) Notice: Subject to any disclaimer, the term of this patent is extended or adjusted under 35 U.S.C. 154(b) by 660 days.

(21) Appl. No.: 18/128,362

(22) Filed: Mar. 30, 2023

(65) Prior Publication Data

US 2023/0242490 A1 Aug. 3, 2023

Related U.S. Application Data

(63) Continuation of application No. PCT/CN2022/086078, filed on Apr. 11, 2022.

(30) Foreign Application Priority Data

Oct. 14, 2021 (CN) .......................... 202111199646.3

(51) Int. Cl.
*C07D 231/36* (2006.01)

(52) U.S. Cl.
CPC .................................. *C07D 231/36* (2013.01)

(58) Field of Classification Search
CPC .................................................... C07D 231/06
See application file for complete search history.

(56) References Cited

U.S. PATENT DOCUMENTS 4,288,602 A 9/1981 Church et al.

FOREIGN PATENT DOCUMENTS

CH 532582 A 1/1973
CN 113929625 A 1/2022

OTHER PUBLICATIONS

International Search Report issued in corresponding International application No. PCT/CN2022/086078, mailed Jun. 23, 2022.
Written Opinion of the International Search Authority in corresponding International application No. PCT/CN2022/086078.

*Primary Examiner* — Paul V Ward
(74) *Attorney, Agent, or Firm* — HOWARD M COHN and Associates, LLC

(57) ABSTRACT

The present disclosure discloses a method for the preparation of sulfinpyrazone, which is produced in two steps with a total yield of 48%, wherein thiophenol as the starting material is electrocatalytically coupled with dichloroethane to obtain 2-chloroethyl phenyl sulfoxide, which then undergoes a substitution reaction with 1,2-diphenyl-3,5-pyrazolidinedione to produce sulfinpyrazone. Compared with the prior art, the present method is characterized by high yield, short steps, less three wastes, good chemical selectivity, no need to use strong bases and oxidants, safe and simple operation, and easy to realize industrial production.

12 Claims, 4 Drawing Sheets

METHOD FOR THE PREPARATION OF SULFINPYRAZONE

TECHNICAL FIELD

The present disclosure relates to the field of drug synthesis, an in particular to a method for the preparation of sulfinpyrazone.

BACKGROUND

The structure of sulfinpyrazone is shown in formula I.

I

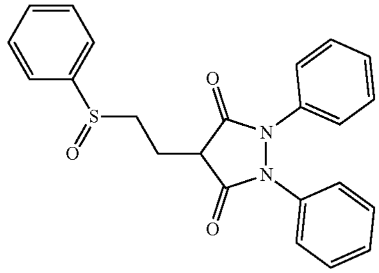

Sulfinpyrazone, a derivative of phenylbutazone, has an eff t of inhibiting platelet aggregation and release in vivo, and can reversibly inhibit platelet prostaglandin synthetase. Sulfinpyrazone can competitively inhibit the active reabsorption of urate at the proximal tubule, increase uric acid excretion, reduce the concentration of uric acid in the blood, and slow or prevent the formation of gouty nodules and articular gouty lesions. It can also inhibit platelet aggregation and increase platelet survival time. It also has a weak anti-inflammatory and analgesic effect.

In the literature *Volumen XLIV, Fasciculus I* 1961, 28, 233. and *Clin. J. Pharm.,* 1999, 30, 100. reported that sulfinpyrazone was synthesized as follows: thiophenol as raw material was reacted with 1,2-dichloroethane, then underwent a nucleophilic substitution reaction with diethyl malonate, followed by a transesterification with diphenylhydrazine, and finally thioether was oxidized to sulfoxide to obtain sulfinpyrazone.

Scheme I. diagram of original research route

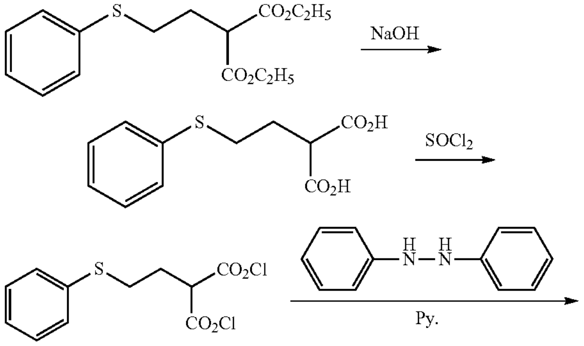

-continued

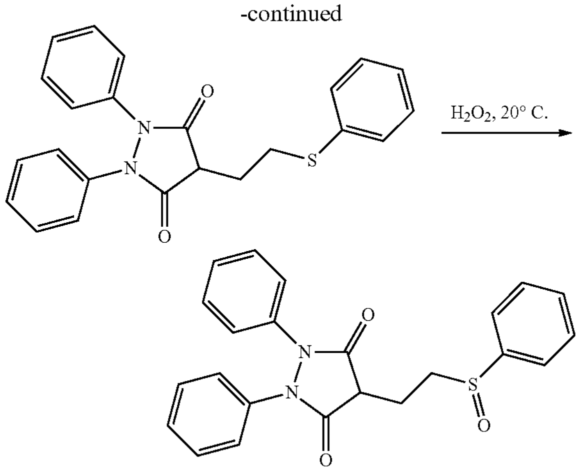

Scheme II. Improved route

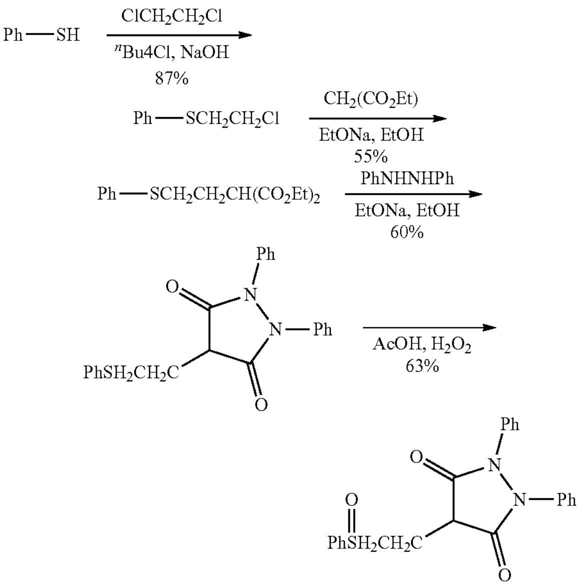

The above two routes have long and tedious steps with low yield. In addition, more importantly, in the last step, thioether is easily over-oxidized to sulfone by the hydrogen peroxide and acetic acid system, so that it is difficult to control the product to remain on the step of obtaining sulfoxide.

In view of the above, since the synthesis route in the prior art not only has long steps and low yield, but also has difficulties in controlling the product retention, ere is an urgent need for a green, easy-to-operate, efficient and fast method to replace the method in the prior art for the preparation of sulfinpyrazone.

SUMMARY

The present disclosure utilizes thiophenol as a raw material produce sulfinpyrazone through two steps: electrocatalytic oxidation and nucleophilic substitution. The method features a shortened process and is environmentally friendly, yielding high purity and stable quality. By eliminating the use of hydrogen peroxide as an oxidant, the method overcomes shortcomings in the prior art where thioether is easily overoxidized to sulfone in classical methods.

The purpose of the present disclosure is to provide a method for the preparation of sulfinpyrazone to solve the above-mentioned problems in the prior art.

In order to achieve the above purpose, the following technical solutions are used in the present disclosure.

A method for the preparation of sulfinpyrazone with the following synthetic routes:

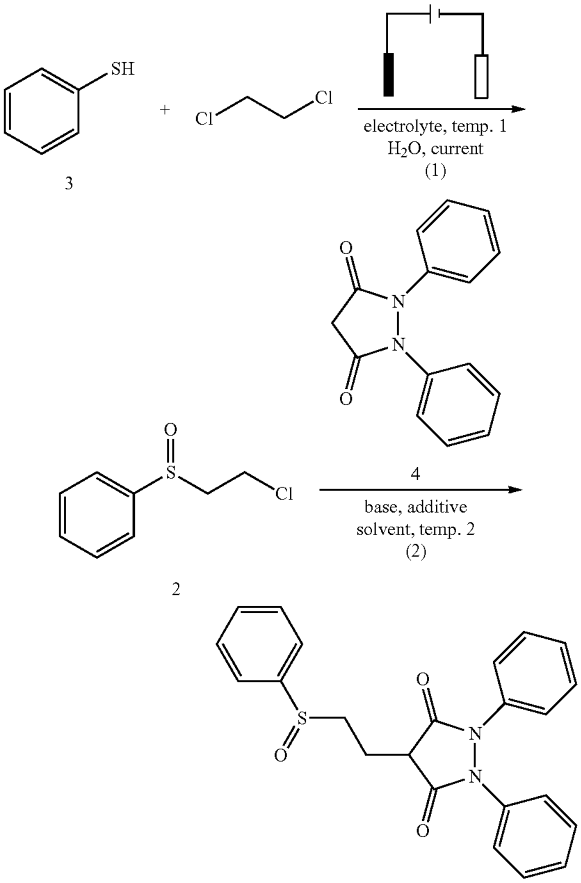

3
2
1 wherein electrolyte represents an electrolyte, current represents a current, temperature represents a temperature, salt represents a salt, base represents a base, additive represents an additive, and solvent represents a solvent.

In one embodiment, the method includes following steps:

(1) dissolving thiophenol as shown in formula 3 and electrolyte in mixed solution of 1,2-dichloroethane and water and reacting by passing the current for 1 to 48 hours to obtain 2-chloroethyl phenyl sulfoxide as shown in formula 2; and (2) mixing and dissolving 2-chloroethyl phenyl sulfoxide as shown in formula 2, 1,2-diphenyl-3,5-pyrazolidinedione as shown in formula 4, the base and the additive in the solvent, and reacting by heating under a nitrogen atmosphere for 1 to 48 hours, md after completing the reaction, subjecting the reaction mixture to column chromatography to obtain sulfinpyrazone as shown in formula 1.

In one embodiment, the anode used in step (1) is selected m one of graphite felt, platinum, and nickel electrodes. The cathode used in step (1) is selected from graphite felt, platinum, nickel, and carbon sheet electrodes, and the electrode specifications are both 1 cm×1 cm.

In one embodiment, the electrolyte in step (1) is any one of tetrabutylammonium bromide, tetrabutylammonium tetrafluoroborate, tetra-n-octylammonium bromide, tetrabutylammonium hexafluorophosphate, lithium perchlorate, ammonium perchlorate, and tetrabutylammonium iodide, and the amount of electrolyte is 0.5-2 times that of thiophenol.

In one embodiment, the water in step (1) is any one of distilled water and deionized water, and the amount thereof is 0.5-10 times that of thiophenol.

In one embodiment, the current in step (1) is 4-30 mA.

In one embodiment, the temperature in step (1) is 30-70° C.; and the amount of 1,2-dichloroethane in step (1) by volume is 5-30 times that of compound 3.

In one embodiment, the solvent in step (2) is selected from one or more of acetone, acetonitrile, and n-hexane.

In one embodiment, the base in step (2) is selected from any one of cesium carbonate, sodium hydroxide, potassium hydroxide, sodium ethoxide, potassium ethoxide, triethylamine, and diisopropylethylamine. The additive is selected from any one of sodium iodide, potassium iodide, lithium iodide, and ammonium iodide. The reaction temperature in step (2) is 50-70° C.

In one embodiment, the amount of the compound 1,2-diphenyl-3,5-pyrazolidinedione in step (2) is 1.0-4.0 times that of 2-chloroethyl phenyl sulfoxide; the amount of base is 1.0-4.0 times that of 2-chloroethyl phenyl sulfoxide; the amount of additive is 1-5 times that of 2-chloroethyl phenyl sulfoxide; and the amount of solvent is 5-10 times that of 2-chloroethyl phenyl sulfoxide.

Compared with the prior art, the present disclosure has the following beneficial effects:

a) introducing a green and environmentally friendly electrochemical method into the synthesis steps, greatly shortening the reaction steps and increasing the overall yield;

b) avoiding the use of strong bases and hydrogen peroxide as an oxidant, improving the atomic economy and reducing environmental pollution; and c) fundamentally overcoming the problem of easy overoxidation of chloroethyl sulfide to chloroethyl sulfone under the hydrogen peroxide system, and improving the selectivity of the reaction. The present method has good application value and potential socio-economic benefits.

DETAILED DESCRIPTION

Figure 1:
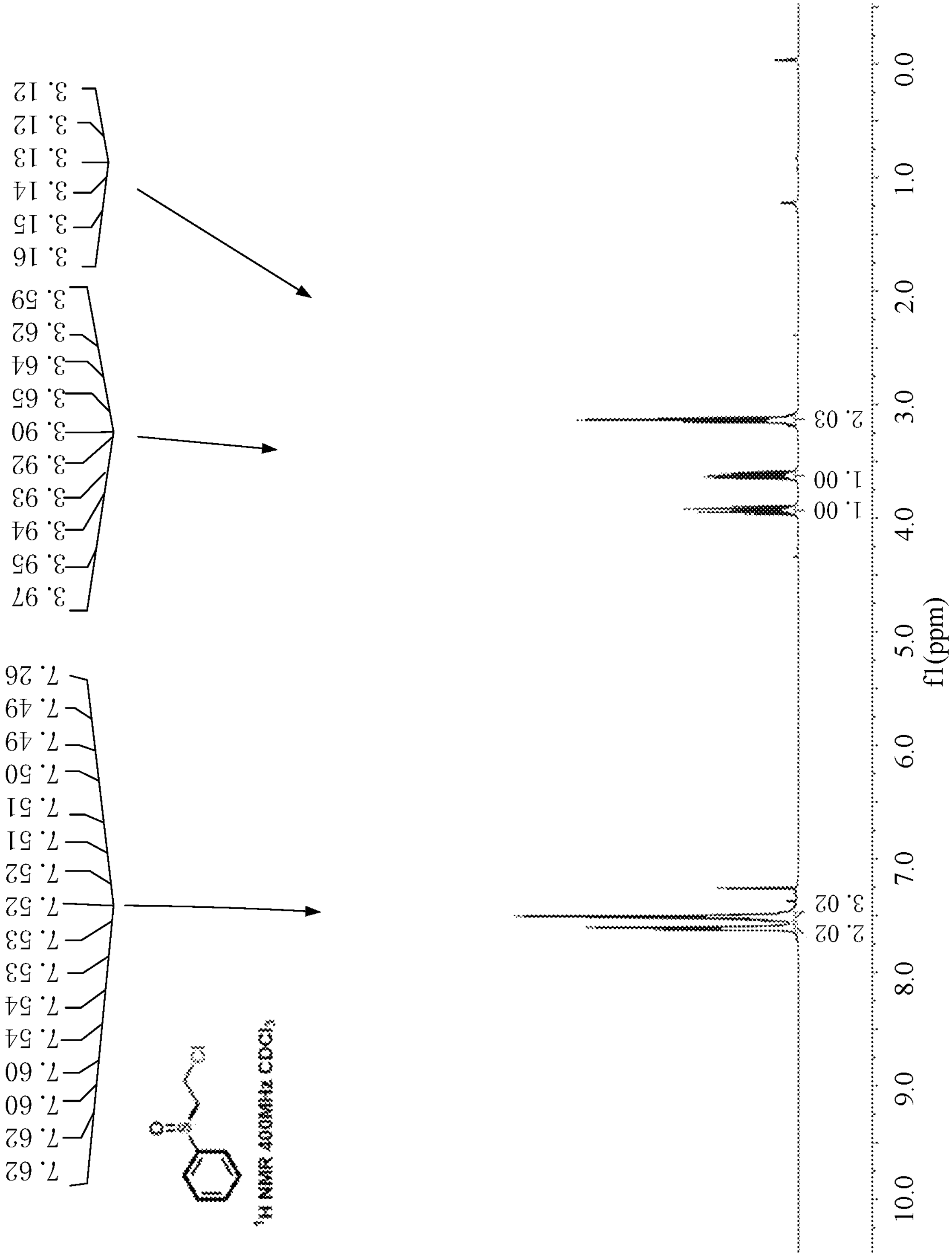
FIG. 1 is a schematic diagram showing the NMR characterization of 2-chloroethyl phenyl sulfoxide 2 of the present disclosure.

In order to make the purpose, technical solutions and advantages of the present disclosure clearer, the following further description of the present disclosure in conjunction with the examples:

A method for the preparation of sulfinpyrazone with the following synthetic routes:

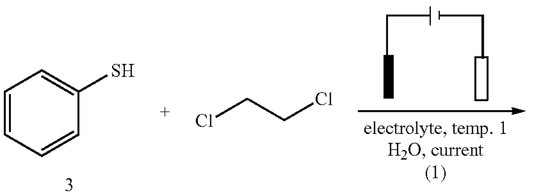

3

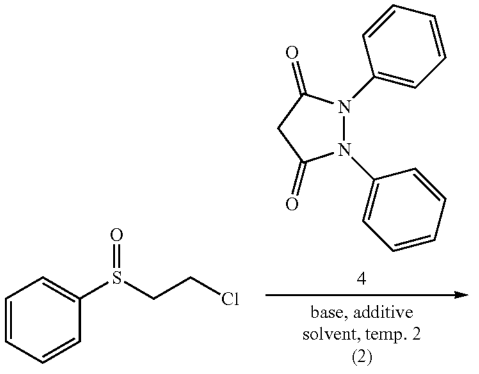

2

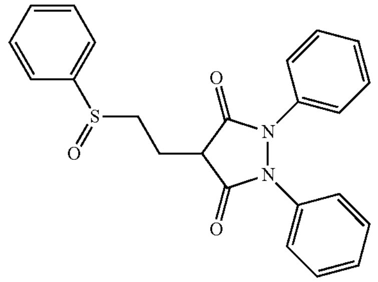

1

The method specifically includes the following steps:

(1) dissolving thiophenol as shown in formula 3 and electrolyte in mixed solution of 1,2-dichloroethane and water and reacting by passing a current for 1 to 48 hours to obtain 2-chloroethyl phenyl sulfoxide as shown in formula 2; and (2) mixing and dissolving 2-chloroethyl phenyl sulfoxide as shown in formula 2, 1,2-diphenyl-3,5-pyrazolidinedione as shown in formula 4, a base and an additive in a solvent, and reacting by heating under a nitrogen atmosphere for 1 to 48 hours, and after completing the reaction, subjecting the reaction mixture to column chromatography to obtain sulfinpyrazone as shown in formula 1.

The anode used in step (1) is selected from one of graphite felt platinum, and nickel electrodes, the cathode used in step (1) is selected from graphite felt, platinum, nickel, and carbon sheet electrodes, and the electrode specifications are both 1 cm×1 cm. The electrolyte in step (1) is any one of tetrabutylammonium bromide, tetrabutylammonium tetrafluoroborate, tetra-n-octylammonium bromide, tetrabutylammonium hexafluorophosphate, lithium perchlorate, ammonium perchlorate, and tetrabutylammonium iodide, and the amount of electrolyte is 0.5-2 times that of thiophenol; the water in step (1) is any one of distilled water and deionized water, and the amount thereof is 0.5-10 times that of thiophenol; the current in step (1) is 4-30 mA; the temperature in step (1) is 30-70° C.; and the amount of 1,2-dichloroethane in step (1) by volume is 5-30 times that of compound 3.

The solvent in step (2) is selected from one or more of acetone, acetonitrile, and n-hexane. The base in step (2) is selected from any one of cesium carbonate, sodium hydroxide, potassium hydroxide, sodium ethoxide, potassium ethoxide, triethylamine, and di propylethylamine. The additive is selected from any one of sodium iodide, potassium iodide, lithium iodide, and ammonium iodide; the reaction temperature in step (2) is 50-70° C. The amount of the compound 1,2-diphenyl-3,5-pyrazolidinedione in step (2) is 1.0-4.0 times that of 2-chloroethyl phenyl sulfoxide; the amount of base is 1.0-4.0 times that of 2-chloroethyl phenyl sulfoxide. The amount of additive is 1-5 times that of 2-chloroethyl phenyl sulfoxide; and the amount of solvent is 5-10 times that of 2-chloroethyl phenyl sulfoxide.

Example 1

2-Chloroethyl phenyl sulfoxide 2 was prepared as follows:

Thiophenol 3 (220.0 mg, 2.0 mmol), tetrabutylammonium tetrafluoroborate (330.0 mg, 1.0 mmol), water (180.0 uL, 10.0 mmol), and 1,2-dichloroethane (4.0) are sequentially added to a reaction flask. The reaction flask is capped with a rubber stopper, and two electrodes are inserted into the reaction flask from the rubber stopper. The two electrodes are respectively a graphite felt anode and a platinum sheet cathode. The reaction is conducted in the reaction flask for 16 hours at a constant current of 20 mA. Upon completion of the reaction, the solvent was removed by distillation under reduced pressure. The residue was mixed with silica gel and subjected to column chromatography using petroleum ether/ethyl acetate (5:1) as the eluent. The method yields 312.0 mg of 2-chloroethyl phenyl sulfoxide 2 as a colorless transparent oily liquid (83% yield).

Figure 2:
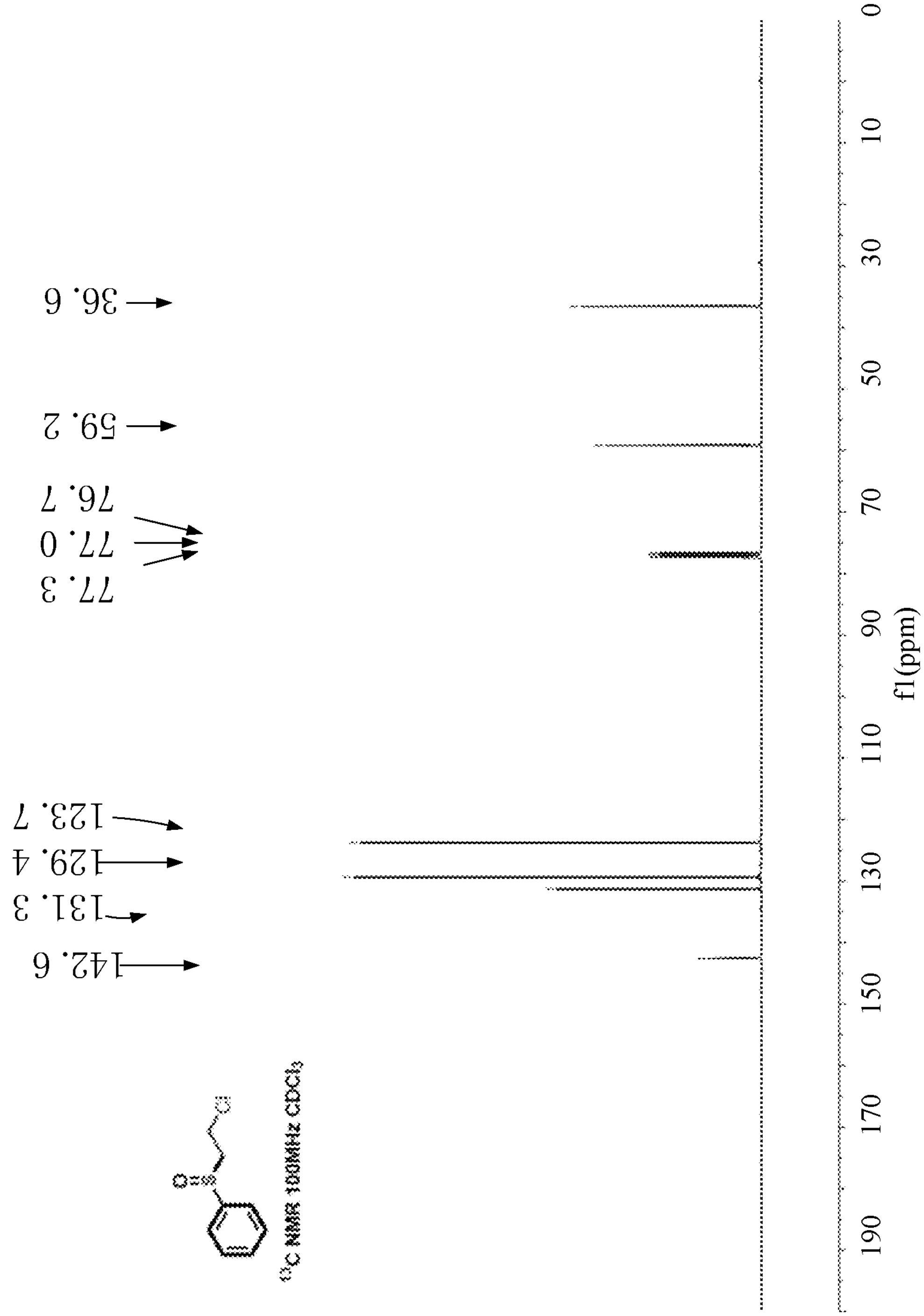
FIG. 2 is another schematic diagram showing the NMR characterization of 2-chloroethyl phenyl sulfoxide 2 of the present disclosure.

NMR characterization of 2-chloroethyl phenyl sulfoxide 2:

The NMR characterization of 2-chloroethyl phenyl sulfoxide 2: is shown in FIGS. 1 and 2.

$^1H$ NMR (400 MHz, $CDCl_3$) δ 7.61 (dd, J=7.6, 2.0 Hz, 2H), 7.54-0.49 (m, 3H), 4.97-3.90 (m, 11H), 3.65-3.59 (m, 1H), 3.16-3.12 (m, 2H). $^{13}C$ NMR (100, $CDCl_3$) δ 142.6, 131.3, 129.4, 123.7, 59.2, 36.6. HRMS (ESI): calcd for $C_8H_{10}ClOS$ $[M+H]^+$ 189.0135, found 189.0126.

Example 2

2-Chloroethyl phenyl sulfoxide 2 was prepared as follows:

Thiophenol 3 (220.0 mg, 2.0 mmol), tetrabutylammonium tetrafluoroborate (330.0 mg, 1.0 mmol), water (180.0 μL, 10.0 mmol), and 1,2-dichloroethane (4.0) are sequentially added to a reaction flask. The reaction flask is capped with a rubber stopper. Two electrodes, which are respectively a graphite felt anode and a platinum sheet cathode, are inserted into the reaction flask through the rubber stopper. The reaction is conducted in the reaction flask at a constant current of 20 mA for 16 hours. Upon completion of the reaction, the solvent is removed via distillation under reduced pressure. The resulting residue is purified by silica gel column chromatography, using a mixture of petroleum ether and ethyl acetate (5:1) as the eluent. The method yields 312.0 mg of 2-chloroethyl phenyl sulfoxide 2 as a colorless, transparent oily liquid (83% yield).

Example 3

2-Chloroethyl phenyl sulfoxide 2 was prepared as follows:

Thiophenol 3 (220.0 mg, 2.0 mmol), tetrabutylammonium bromide (332.0 mg, 1.0 mmol), water (180.0 $\mu$L, 10.0 mmol), and 1,2-dichloroethane (0.0 mL) are sequentially added into a reaction flask. The reaction flask is sealed with a rubber stopper equipped with a graphite felt anode and a platinum sheet cathode. The reaction is conducted in the reaction flask at a constant current of 20 mA for 16 hours. Upon completion of the reaction, the solvent is removed via distillation under reduced pressure. The resulting residue is purified by silica gel column chromatography using a mixture of petroleum ether and ethyl acetate (5:1) as the eluent. 2-chloroethyl phenyl sulfoxide 2 (203.0 mg) is obtained as a colorless transparent oily liquid in 54% yield.

Example 4

2-Chloroethyl phenyl sulfoxide 2 was prepared as follows:

Thiophenol 3 (220.0 mg, 2.0 mmol), tetrabutylammonium tetrafluoroborate (330.0 mg, 1.0 mmol), water (180.0 uL, 10.0 mmol), and 1,2-dichloroethane (4.0) are sequentially added to a reaction flask. The flask is capped with a rubber stopper equipped with a graphite felt anode and a platinum sheet cathode. The reaction is carried out in the reaction flask for 16 hours at a constant current of 10 mA. Upon completion of the reaction, the solvent is removed by distillation under reduced pressure. The resulting residue is purified by column chromatography on silica gel, using a mixture of petroleum ether and ethyl acetate (5:1) the eluent. The method yields 229.3 mg of 2-chloroethyl phenyl sulfoxide 2 as a colorless transparent oily liquid (61% yield).

Sulfinpyrazone 1 in step 2) is prepared as shown in Examples to 9:

Example 5

2-Chloroethyl phenyl sulfoxide 2 (189.0 mg, 1.0 mmol), 1,2-diphenyl-3,5-pyrazolidinedione 4 (378.2 mg, 1.5 mmol), cesium carbonate (488.7 mg, 1.5 mmol), sodium iodide (149.9 mg, 1.0 mmol), and acetone (6 mL) are sequentially added to a three-necked flask. Openings of the three-necked flask are respectively capped with a co denser tube, a three-way stopcock with inert gas balloon, and a rubber stopper for nitrogen replacement. The mixture is refluxed at 65° C. for 12 hours. Upon completion of the reaction, acetone is removed by distillation under reduced pressure, and resulting residue is dissolved in appropriate amount of water to obtain a solution. The pH of the solution is adjusted to 5-6 by adding 10% dilute hydrochloric acid, followed by extraction with ethyl acetate (10 mL×3). The organic layers are combined, dried over anhydrous sodium sulfate, and concentrated by removing the solvent under reduced pressure. The residue is purified by column chromatography on silica gel, using a mixture of dichloromethane and ethyl acetate (10:1) as the eluent. The process yields 234.6 mg of sulfinpyrazone 1 as a white solid (58% yield).

NMR Characterization of Sulfinpyrazone 1

Figure 3:
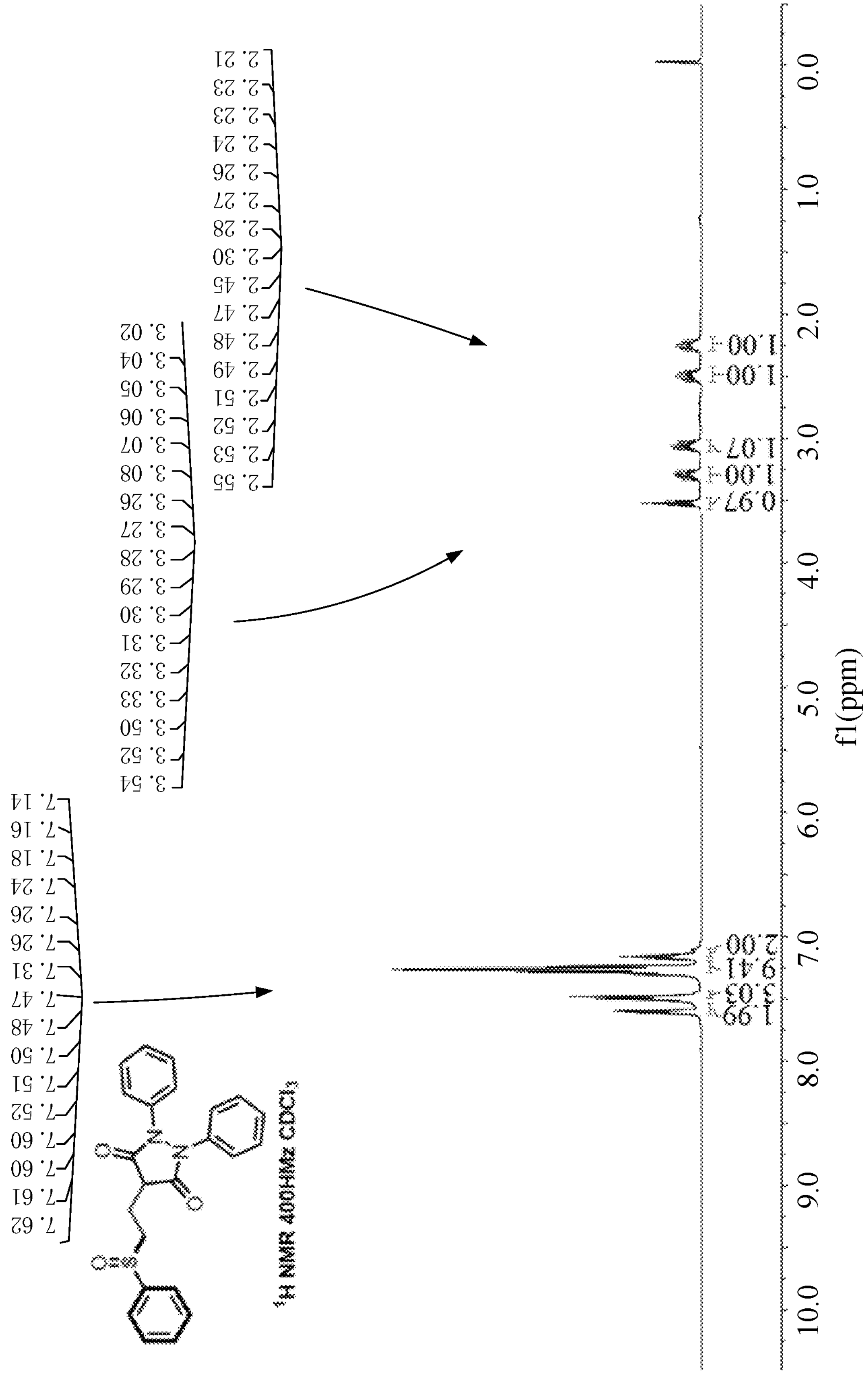
FIG. 3 is a schematic diagram showing the NMR characterization of sulfinpyrazone 1 of the present disclosure.
Figure 4:
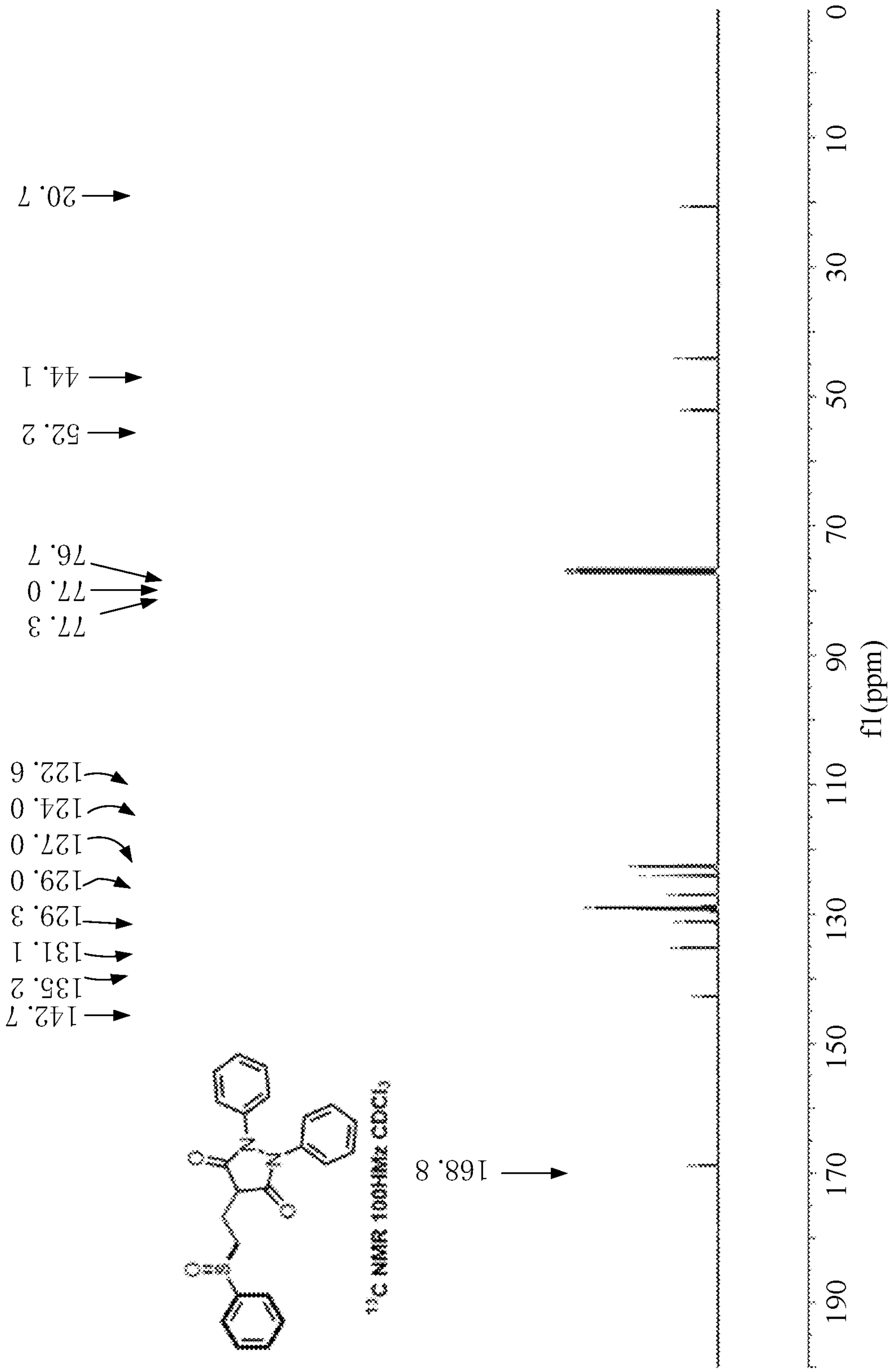
FIG. 4 is another schematic diagram showing the NMR characterization of sulfinpyrazone 1 of the present disclosure.

The NMR characterization of sulfinpyrazone 1: is shown in FIGS. 3 and 4.

$^1$H NMR (400 MHz, CDCl3) δ 7.61 (dd, J=7.6, 1.6 Hz, 2H), 7.2-7.47 (m, 3H), 7.31-7.24 (m, 9H), 7.16 (t, J=6.8 Hz, 2H), 3.52 (t, J=7.4 Hz, 1H), 3.33-3.26 (m, 1H), 3.09-3.02 (m, 1H), 2.55-2.45 (m, 1H), 2.23-2.20 (m, 1H). $^{13}$C NMR (100 $CDCl_3$) δ 168.8, 142.7, 135.2, 131.1, 129.3, 129.0, 127.0, 124.0, 122.6, 52.2, 44.1, 20.7. HRMS (ESI): calcd for $C_{23}H_{21}N_2O_3S$ $[M+H]^+$ 405.1267, found 405.1261.

Example 6

2-Chloroethyl phenyl sulfoxide 2 (189.0 mg, 1.0 mmol), 1,2-diphenyl-3,5-pyrazolidinedione 4 (302.6 mg, 1.2 mmol), cesium carbonate (391.0 mg, 1.2 mmol), sodium iodide (149.9 mg, 1.0 mmol), and acetone (6 mL) are sequentially added to a three-necked flask.

Openings of the three-necked flask flask are respectively capped with condenser tube, a three-way stopcock with inert gas balloon, and a rubber stopper for nitrogen replacement. The mixture is refluxed at 65° C. for 12 hours. Upon completion of the reaction, acetone is removed by distillation under reduced pressure, and the resulting residue is dissolved in an appropriate amount of water. The pH of the solution is adjusted to 5-6 by adding 10% dilute hydrochloric acid, followed by extraction with ethyl acetate (10 mL×3). The organic layers are combined, dried over anhydrous sodium sulfate, and concentrated by removing the solvent under reduced pressure. The residue is purified by column chromatography on silica gel, using a mixture of dichloromethane and ethyl acetate (10:1) as the eluent. The process yields 165.8 mg of sulfinpyrazone 1 as a white solid (41% yield).

Example 7

2-Chloroethyl phenyl sulfoxide 2 (189.0 mg, 1.0 mmol), 1,2-diphenyl-3,5-pyrazolidinedione 4 (302.6 mg, 1.2 mmol), cesium carbonate (391.0 mg, 1.2 mmol), sodium iodide (224.8 mg, 1.5 mmol), and acetone (6 mL) are sequentially added to a three-necked flask. Openings of the three-necked flask are respectively capped with a condenser tube, a three-way stopcock with inert gas balloon, and a rubber stopper on the other side or nitrogen replacement. The mixture is refluxed at 65° C. for 12 hours. Upon completion of the reaction, acetone is removed by distillation under reduced pressure, and the resulting residue is dissolved in an appropriate amount of water. The pH of the solution is adjusted to 51.6 by adding 10% dilute hydrochloric acid, followed by extraction with ethyl acetate (10 mL×3). The organic layers are combined, dried over anhydrous sodium sulfate, and concentrated by removing the solvent under reduced pressure. The residue is purified by column chromatography on silica gel, using a mixture of dichloromethane and ethyl acetate (10:1) as the eluent. This process yields 202.2 mg of sulfinpyrazone 1 as a white solid (50% yield).

Example 8

2-Chloroethyl phenyl sulfoxide 2 (189.0 mg, 1.0 mmol), 1,2-diphenyl-3,5-pyrazolidinedione 4 (378.2 mg, 1.5 mmol), cesium carbonate (488.7 g, 1.5 mmol), potassium iodide (166.0 mg, 1.0 mmol), and acetone (6 mL) are sequentially add to a three-necked flask. Openings of the three-necked flask are respectively equipped with a condenser tube, a three-way stopcock with inert gas balloon, and a rubber stopper for nitrogen replacement. The mixture is refluxed at 65° C. for 12 hours. At the end of the reaction, acetone is removed by distillation under reduced pressure, and the resulting residue is dissolved in an appropriate amount of water. The pH of the solution is adjusted to 5-6 by adding 10% dilute hydrochloric acid, followed by extraction with ethyl acetate (10 mL×3). The organic layers are combined, dried over anhydrous sodium sulfate, and concentrated by removing the solvent under reduced pressure. The residue is purified by column chromatography on silica gel, using a mixture of dichloromethane and ethyl acetate (10:1) as the eluent. The process yields 194.2 mg of sulfinpyrazone 1 as a white solid (48% yield).

Example 9

2-Chloroethyl phenyl sulfoxide 2 (189.0 mg, 1.0 mmol), 1,2-diphenyl-3,5-pyrazolidinedione 4 (378.2 mg, 1.5 mmol), cesium carbonate (488.7 g, 1.5 mmol), sodium iodide (149.9 mg, 1.0 mmol), and acetonitrile (6 mL) are sequentially added to a three-necked flask. Openings of the flask are respectively capped with a condenser tube, a three-way stopcock with inert gas balloon, and a rubber stopper for nitrogen replacement e mixture is refluxed at 65° C. for 12 hours. Upon completion of the reaction, the solvent is removed by distillation under reduced pressure, and the resulting residue is dissolved in an appropriate amount of water. The pH of the solution is adjusted to 5-6 by adding 10% dilute hydrochloric acid, followed by extraction with ethyl acetate (10 mL×3). The organic layers are combined, dried over anhydrous sodium sulfate, and concentrated by removing the organic solvent under reduced pressure. The residue is purified by column chromatography on silica gel, using a mixture of dichloromethane and ethyl acetate (10:1) as the eluent. This process yields 125.4 mg of sulfinpyrazone 1 as a white solid (31% yield*).

It can be seen from the above that in the technical solution of the present disclosure, Examples 1 to 4 are the preparation of 2-chloroethyl phenyl sulfoxide in step 1, an Examples 5 to 9 are the preparation of sulfinpyrazone from 2-chloroethyl phenyl sulfoxide in step 1 in step 2. Compared with the prior art, introduction of a green and environmentally friendly electrochemical method into the synthesis steps not only greatly shortens the reaction steps, but also increases the overall yield; the use of strong bases and hydrogen peroxide as an oxidant is avoided, the atomic economy is improved, and the environmental pollution is reduced; and the problem of easy over-oxidation of chloroethyl sulfide to chloroethyl sulfone under the hydrogen peroxide system is overcome fundamentally, and the selectivity of the reaction is improve. The preparation route according to the present disclosure has short steps, the yield of step 1) can reach up to 83%, and the yield of step 2) can reach up to 58% (see Example 5).

The above description is only a preferred embodiment according to the present disclosure, not thereby limiting the patent scope according to the present disclosure, and all equivalent transformations made by the present disclosure are within the scope of patent protection of the present invention.

What is claimed is:

1. A method for a preparation of sulfinpyrazone, wherein comprising following synthetic routes:

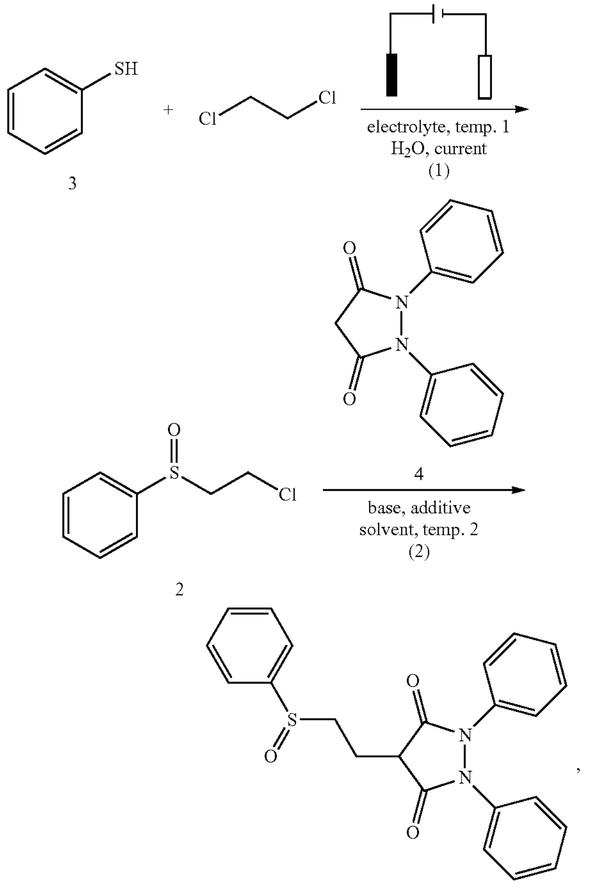

1 wherein electrolyte represents an electrolyte, current represents a current, temperature represents a temperature, salt represents a salt, base represents a base, additive represents an additive, and solvent represents a solvent.

2. The method according to claim 1, wherein the method comprises following steps:

(1) dissolving thiophenol shown in formula 3 and electrolyte in a mixed solution of 1,2-dichloroethane and water and reacting by passing the current for 1 to 48 hours to obtain 2-chloroethyl phenyl sulfoxide shown in formula 2; and (2) mixing and dissolving 2-chloroethyl phenyl sulfoxide shown in formula 2, 1,2-diphenyl-3,5-pyrazolidinedione shown in formula 4, the base and the additive in the solvent, and reacting by heating under a nitrogen atmosphere for 1 to 48 hours, and after a reaction is completed, subjecting A reaction mixture to column chromatography to obtain sulfinpyrazone shown in formula 1.

3. The method according to claim 1, wherein an anode used in step (1) is selected from one of a group consisting of graphite felt, platinum, and nickel electrodes, and a cathode used in step (1) is selected from a group consisting of graphite felt, platinum, nickel, and a specification of each of the anode and the cathode is 1 cm*1 cm.

4. The method according to claim 1, wherein an anode used in step (1) is selected from one of a group consisting of graphite felt, platinum, and nickel electrodes, and a cathode used in step (1) is selected from a group consisting of graphite felt, platinum, nickel, and a specification of each of the anode and the cathode is 1 cm*1 cm.

5. The method according to claim 2, wherein the electrolyte in step (1) is any one of tetrabutylammonium bromide, tetrabutylammonium tetrafluoroborate, tetra-n-octylammonium bromide, tetrabutylammonium hexafluorophosphate, lithium perchlorate, ammonium perchlorate, and tetrabutylammonium iodide, and an amount of electrolyte is 0.5-2 times that of thiophenol.

6. The method according to claim 2, wherein the water in step (1) is any one of distilled water and deionized water, and an amount thereof is 0.5-10 times that of thiophenol.

7. The method according to claim 2, wherein the current in step (1) is 4-30 mA.

8. The method according to claim 2, wherein the temperature in step (1) is 30-70° C.; and a volume of 1,2-dichloroethane in step (1) is 5-30 times that of compound 3.

9. The method according to claim 1, wherein the solvent in step (2) is selected from one or more of acetone, acetonitrile, and n-hexane.

10. The method according to claim 2, wherein the solvent in step (2) is selected from one or more of acetone, acetonitrile, and n-hexane.

11. The method according to claim 2, wherein the base in step (2) is selected from any one of cesium carbonate, sodium hydroxide, potassium hydroxide, sodium ethoxide, potassium ethoxide, triethylamine, and diisopropylethylamine; the additive is selected from any one of sodium iodide, potassium iodide, lithium iodide, and ammonium iodide; and a reaction temperature in step (2) is 50-70° C.

12. The method according to claim 2, wherein an amount of 1,2-diphenyl-3,5-pyrazolidinedione in step (2) is 1.0-4.0 times that of 2-chloroethyl phenyl sulfoxide; an amount of base is 1.0-4.0 times that of 2-chloroethyl phenyl sulfoxide; an amount of additive is 1-5 times that of 2-chloroethyl phenyl sulfoxide; and an amount of the solvent is 5-10 times that of 2-chloroethyl phenyl sulfoxide.

* * * * *